United States Patent [19]
Maas

[11] Patent Number: 5,810,749
[45] Date of Patent: Sep. 22, 1998

[54] NASAL FIXATION WITH WATER-HARDENING FIBER-MESH RESIN

[76] Inventor: Corey S. Maas, 130 Currey Ave., Sausalito, Calif. 94965

[21] Appl. No.: 646,825

[22] Filed: May 21, 1996

[51] Int. Cl.⁶ ..................................................... A61F 5/01
[52] U.S. Cl. .................................. 602/6; 602/8; 264/222
[58] Field of Search .................................. 602/5, 6, 8, 17; 128/857, 858, 97.1; 264/222, DIG. 30

[56] References Cited

U.S. PATENT DOCUMENTS

| | | | |
|---|---|---|---|
| 3,426,751 | 2/1969 | Radewan | 128/858 |
| 4,213,452 | 7/1980 | Shippert | 128/858 |
| 4,376,438 | 3/1983 | Straube et al. . | |
| 4,427,002 | 1/1984 | Baron et al. | 602/6 |
| 4,433,680 | 2/1984 | Yoon . | |
| 4,502,479 | 3/1985 | Garwood et al. . | |
| 4,609,578 | 9/1986 | Reed . | |
| 4,652,493 | 3/1987 | Reichmann et al. . | |
| 4,667,661 | 5/1987 | Scholz et al. . | |
| 4,668,563 | 5/1987 | Buese et al. . | |
| 4,705,840 | 11/1987 | Buckanin . | |
| 4,774,937 | 10/1988 | Scholz et al. . | |
| 4,800,872 | 1/1989 | Buese et al. . | |
| 4,898,159 | 2/1990 | Buese et al. . | |
| 5,022,389 | 6/1991 | Brennan . | |
| 5,090,405 | 2/1992 | Jansen et al. . | |
| 5,273,802 | 12/1993 | Scholz et al. . | |
| 5,370,927 | 12/1994 | Scholz et al. . | |
| 5,382,445 | 1/1995 | Yasis . | |
| 5,403,267 | 4/1995 | Pearce et al. . | |
| 5,423,735 | 6/1995 | Callinan et al. . | |
| 5,449,550 | 9/1995 | Yasis et al. . | |
| 5,455,060 | 10/1995 | Neamy et al. . | |
| 5,461,885 | 10/1995 | Yokoyama et al. . | |
| 5,468,219 | 11/1995 | Crippen . | |
| 5,474,522 | 12/1995 | Scholz et al. . | |
| 5,476,440 | 12/1995 | Edenbaum . | |
| 5,480,708 | 1/1996 | Cheng . | |

*Primary Examiner*—Richard J. Apley
*Assistant Examiner*—Kim M. Lee
*Attorney, Agent, or Firm*—Townsend and Townsend and Crew LLP

[57] ABSTRACT

Nasal bones are fixed in place after surgery or injury by the placement of a casting material over the outer surface of the nose, precut to conform to the dimensions of the nose. The casting material is a resin-impregnated fibrous sheet, the resin being curable to a hardened form upon exposure to atmospheric moisture. The resin-impregnated fibrous sheet is similar in chemical composition to casting tapes used for long-bone fractures where the tapes are wrapped around a limb that has been encased in a padding material.

10 Claims, No Drawings

NASAL FIXATION WITH WATER-HARDENING FIBER-MESH RESIN

This invention relates to nasal casts for fixation of the bones of a patient's nose following trauma to the nose such as that resulting from surgery or injury.

BACKGROUND OF THE INVENTION

Corrective shaping of the nose is a common part of treatments to correct both internal and external nasal deformities, both for therapeutic and cosmetic reasons. As the nose and its internal bone structure heals, the nose must be protected and immobilized to maintain its the desired shape and symmetry. Various nasal splints and casts have been devised for this purpose, but these are generally difficult to use and poorly adaptable to the varying sizes and contours encountered among individual patients, if at all, or they are slow to harden and require multiple layers or applications.

SUMMARY OF THE INVENTION

The present invention resides in the use of a fibrous substrate impregnated with a water-hardenable resin, preshaped to cover substantially only the nose, as a nasal cast. Prior to this invention, impregnated substrates of this type have been used as casting tapes for extremities, limbs and long-bone fractures. These tapes have been used for wrapping around a body member, using approximately twelve to fifteen layers of the tape to form a thick continuous cast. In use, the tape is applied over a compressible padding material that accommodates swelling of the body member. In contrast to these previous uses, usage of the impregnated substrate in accordance with the present invention is limited to the nose, and far fewer layers are used, without wrapping and without the use of underlying padding. Advantages offered by this invention are its ease of use relative to existing nasal casts and splints, the ability to mold the substrate to the precise contours of the nose to which it is applied, and the rapid hardening of the resin to form a firm protective cast. This invention further utilizes the tacky surface quality of the resin prior to hardening as a means of retaining the impregnated substrate in place as it hardens.

Further features and advantages of the invention will be apparent from the description that follows.

DETAILED DESCRIPTION OF THE INVENTION AND PREFERRED EMBODIMENTS

Water-hardenable resins of a wide variety of chemical formulae and combinations can be used in the practice of this invention. Preferred such resins are those that cure to polyurethanes. The principal resins of this class are mixtures that include an isocyanate prepolymer and a polyol, optionally with a catalyst also present.

Suitable isocyanate prepolymers include both aromatic and nonaromatic polyisocyanates. Examples are toluene diioscyanate (TDI), hexamethylene diioscyanate (HDI), polymethylene polyphenyl diisocyanate (PMDI), 4,4'-methylenebis(phenyl isocyanate) (MDI), isophorone diisocyanate (IPDI), meta-xylylene diisocyanate (XDI), 1,3-bis(isocyanatomethyl)cyclohexane ($H_6DI$), 1,4-bis(isocyanatomethyl)cyclohexane (BDI), and various substituted analogs of these compounds.

Suitable polyols include both polyester polyols and polyether polyols. Examples of polyether polyols are poly (ethylene glycol), poly(propylene glycol), and poly (tetramethylene glycol). Examples of polyester polyols are the reaction products of polybasic acids such as adipic acid, phthalic acid, hexahydrophthalic acid, and caprolactone, with glycols such as ethylene glycol, propylene glycol, diethylene glycol, dipropylene glycol, 1,4-butanediol, 1,6-hexanediol, glycerol, trimethylolpropane, and 1,1,1-trimethylolethane. Polyols containing amine nitrogens are also included, for example: N-methyldiethanolamine, N-ethyldiethanolamine, N-methyldipropanolamine, triethanolamine, and tripropanolamine.

The resin will optionally contain a catalyst selected from any of the species known for their ability to catalyze polyurethane formation. Tertiary amines are of particular interest. Examples are 1,4-diazabicyclo[2.2.2]octane (triethylenediamine), azabicyclo[2.2.2]octane, 1,8-diazabicyclo[5.3.0]undec-7-ene, 4-{2-[1-methyl-2-(4-morpholinyl)ethoxy]ethyl}morpholine. Di-n-butyltin diacetate is an example of a non-amine catalyst. The latter can be used either alone or in combination with a tertiary amine.

The impregnant may further contain additional components such as binders to facilitate adherence of the resin to the fibrous substrate. These and other components will be readily apparent to those skilled in the art, as the same components used in casting tapes of the prior art used for wrapping injured limbs for long bone fractures.

Resin mixtures of the above description are inherently tacky, as are the fibrous materials impregnated with these resins. This tacky character causes the impregnated substrate to adhere to the patient's skin and to remain so while the resin hardens. In accordance with this invention, it is preferred not to include additives that reduce or eliminate the tacky character of the resins. Once the resin hardens, an adhesive tape can be applied along the edges of the cast to further secure it to the patient's nose.

Materials suitable for use as the fibrous substrate in this invention include nonwoven, woven or knitted fabrics, preferably air-permeable, preferably with a weight per unit area of about 20 to 500 $g/m^2$, depending on the type of fabric, and, for woven and knitted fabrics, preferably with a thread count of 2 to 20 threads per linear centimeter in both the longitudinal and transverse directions. Illustrative fibrous materials are fiber glass, polyaramide, polypropylene, and polyester, or blends of these materials or of these materials with elastic fibers such as ethylene-propylene rubber.

The impregnated fibrous substrate (uncured casting material) of the present invention is substantially trapezoidal in shape to cover the outer surface of the patient's nose, and optionally with lateral regions of relatively small area to extend slightly onto the facial surface at the locations adjacent to the nose. It is contemplated that the impregnated fibrous substrate will be precut to this shape and packaged in a moisture-free, air- and moisture-impermeable package to avoid all contact with moisture while still in the package. The package can be any conventional material that is air- and moisture-impermeable. Examples are various polymeric materials and metal foils, including laminates. The package serves as a kit and includes, either on its exterior or as an insert inside the package, instructions and directions for use of the material on the nose, optionally including one or more of the following: the types of procedures performed on the nose that will benefit from the subsequent application of the casting material, instructions for how to assure that the material is properly sized to fit the nose, instructions for how to position the material over the nose together with any protective underlying layers, and how many layers to use (generally 4 or 5). The kit will further contain adhesive tape to serve as a protective underlying layer (as discussed more fully below). The kit will be packaged in a sterile manner, in addition to being sealed against atmospheric moisture.

The uncured casting material is contemplated to be made available in a range of sizes to fit individual patients. In general, the shorter of the two parallel sides (which will lie transverse to the nose at the top of the nose) will preferably range from about 20 mm to about 50 mm in length, most preferably from about 25 mm to about 40 mm. The longer of the two parallel sides (which will lie transverse to the nose at the bottom) will range from about 40 mm to about 100 mm in length, most preferably from about 50 mm to about 75 mm, provided that the lower side always exceeds the upper side in length by at least about 20 cm. Rather than parallel to the upper side, the longer of the two transverse edges can also be curved or in the shape of a shallow V. The two nonparallel sides forming the remainder of the trapezoid will preferably range from about 30 mm to about 75 mm in length each, most preferably from about 40 mm to about 60 mm. The angle between one of the nonparallel sides and a line perpendicular to the parallel sides is preferably from about 10° to about 45°, and most preferably from about 15° to about 30°. The corners of the trapezoid can be sharp corners or rounded, although rounded corners are preferred since they will minimize discomfort to or scratching of the patient as the casting material cures.

In the practice of this invention, the casting material will be applied to the nose in sterile condition and in fewer layers than the prior art. While as little as one layer can be used, preferred applications will involve the use of two to eight layers, and preferably three to five layers. A presently preferred method of use is the application of four layers. All layers can be of the same shape and size.

A layer of tape or other protective material can be applied directly to the patient's skin underneath the casting material to shield the skin from the resin components, if desired. Any conventional tape designed for clinical use can be used, preferably a hypoallergenic tape with adhesive on one side only. The tape is preferably preshaped to a shape substantially identical to that of the uncured casting material. The sole purpose of the tape is to act as a barrier between the resin and the skin. No padding of any kind is contemplated in the tape construction or in any form between the skin and the resin-impregnated fibrous material.

The foregoing is offered primarily for purposes of illustration. It will be readily apparent to those skilled in the art that the materials, compositions, and configurations described herein can be further modified or substituted in various ways without departing from the spirit and scope of the invention.

I claim:

1. A method for fixation of nasal bones after trauma or surgery, comprising:

(a) applying to the outer surface of a patient's nose a sheet of a fibrous substrate impregnated with a water-hardenable resin and pre-shaped to cover substantially only the nose, in the absence of any compressible layers intervening between the substrate and the patient's nose; and (b) permitting said resin to harden by exposure to atmospheric moisture.

2. A method in accordance with claim 1 in which said substrate thus impregnated with said resin is tacky in surface character, thereby causing said substrate to adhere to the patient's nose prior to hardening.

3. A method in accordance with claim 1 further comprising placing a layer of non-compressible skin-protective tape between said substrate and said patient's nose.

4. A method in accordance with claim 1 in which said substrate is substantially trapezoidal in shape.

5. A method in accordance with claim 1 in which said water-hardenable resin is a composition that cures to a polyurethane upon activation by water.

6. A method in accordance with claim 1 in which said fibrous substrate is an open-weave, air-permeable material.

7. A method in accordance with claim 1 in which (a) comprises applying from two to eight of said sheets.

8. A method in accordance with claim 1 in which (a) comprises applying from three to six of said sheets.

9. A kit for forming a nasal cast, comprising:

(a) a plurality of sheets of a fibrous substrate impregnated with a water-hardenable resin, each said sheet pre-shaped to cover substantially only the nose, said sheets sealed in a sterile, moisture-free, air-impermeable and moisture-impermeable package; and (b) printed matter comprising instructions for use of said sheets as a nasal cast by application to the nose of a patient.

10. A kit in accordance with claim 9, further comprising:

(c) non-compressible skin-protective tape precut in a shape substantially identical to that of said sheets of impregnated fibrous substrate.

* * * * *